(12) United States Patent
Fujikawa et al.

(10) Patent No.: US 8,119,850 B2
(45) Date of Patent: Feb. 21, 2012

(54) PROCESS FOR PRODUCING UNSATURATED HYDROCARBON COMPOUND

(75) Inventors: Shinjiro Fujikawa, Chiba (JP); Takuji Okamoto, Chiba (JP); Kiyohiko Yokota, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 991 days.

(21) Appl. No.: 11/815,975

(22) PCT Filed: Feb. 15, 2006

(86) PCT No.: PCT/JP2006/302606
§ 371 (c)(1),
(2), (4) Date: Aug. 10, 2007

(87) PCT Pub. No.: WO2006/088038
PCT Pub. Date: Aug. 24, 2006

(65) Prior Publication Data
US 2009/0030255 A1    Jan. 29, 2009

(30) Foreign Application Priority Data

Feb. 21, 2005 (JP) ................................. 2005-044853

(51) Int. Cl.
*C07C 2/22* (2006.01)
(52) U.S. Cl. ........ 585/512; 585/502; 585/510; 585/511; 585/520; 585/521; 585/523
(58) Field of Classification Search .................. 585/510, 585/511, 512, 502, 520, 521, 523
See application file for complete search history.

(56) References Cited

U.S. PATENT DOCUMENTS

| | | | | |
|---|---|---|---|---|
| 4,658,078 A | * | 4/1987 | Slaugh et al. ................. | 585/512 |
| 5,087,788 A | * | 2/1992 | Wu ................. | 585/512 |
| 5,321,189 A | * | 6/1994 | Mueller et al. ................. | 585/512 |
| 5,527,930 A | * | 6/1996 | Sangokoya ................. | 556/179 |
| 5,625,106 A | * | 4/1997 | Marks et al. ................. | 585/512 |
| 6,153,550 A | * | 11/2000 | Kissin ................. | 502/103 |
| 6,214,760 B1 | * | 4/2001 | Chen et al. ................. | 502/103 |
| 2001/0041817 A1 | * | 11/2001 | Bagheri et al. ................. | 585/517 |
| 2005/0143254 A1 | * | 6/2005 | Sangokoya et al. ................. | 502/152 |

FOREIGN PATENT DOCUMENTS

| | | |
|---|---|---|
| JP | 05 039229 | 2/1993 |
| JP | 08 027037 | 1/1996 |
| JP | 8 34749 | 2/1996 |
| JP | 10 087518 | 4/1998 |
| JP | 2002 508402 | 3/2002 |
| WO | 2005 066191 | 7/2005 |

OTHER PUBLICATIONS

U.S. Appl. No. 11/816,366, filed Aug. 15, 2007, Yokota, et al.

* cited by examiner

*Primary Examiner* — In Suk Bullock
*Assistant Examiner* — Bradley Etherton
(74) *Attorney, Agent, or Firm* — Oblon, Spivak, McClelland, Maier & Neustadt, L.L.P.

(57) ABSTRACT

Disclosed is a method for producing an unsaturated hydrocarbon compound wherein an α-olefin is dimerized by using a catalyst system composed of a metallocene compound (A) and an oxygen-containing organometallic compound modified with a halogen-containing compound (B). By this method, an unsaturated hydrocarbon compound having unsaturated double bonds in a high ratio, in particular the one having a terminal vinylidene group can be produced efficiently.

10 Claims, No Drawings

PROCESS FOR PRODUCING UNSATURATED HYDROCARBON COMPOUND

CROSS REFERENCE TO RELATED APPLICATION

This application is a 371 of PCT/JP06/302606, filed on Feb. 15, 2006, and claims priority to Japanese Patent Application No. 2005-044853, filed on Feb. 21, 2005.

TECHNICAL FIELD

The present invention relates to an efficient method for producing an unsaturated hydrocarbon compound useful as a lubricant, cleaning agent, additive, its intermediate or the like.

BACKGROUND ART

Dimerization reaction of an α-olefin using a catalyst composed of a combination of a metallocene, an aluminoxane, an organoaluminum compound and the like is publicly known, and examples of such catalyst include a catalyst composed of zirconocene and methylaluminoxane (for example, Patent Document 1), a catalyst composed of zirconocene, alkylaluminoxane, trimethylaluminum (for example, Patent Document 2) and others.

Moreover, oligomerization of an α-olefin is also publicly known, for which a catalyst composed of zirconocene, organoaluminum and borate (for example, Patent Document 3), a catalyst composed of zirconocene, organoaluminum and borane (for example, Patent Document 4), a catalyst composed of zirconocene, methylaluminoxane, and organoaluminum (for example, Patent Document 5), and the like are used.

However, as activity of those catalyst systems are low and a large amount of the catalyst is required, productivity is inferior, and therefore, industrial utilization is difficult.

Furthermore, addition of hydrogen to dimerization and oligomerization reaction systems is not known.

In a polymerization reaction using a metallocene catalyst, hydrogen is added to control the molecular weight of the polymer.

This is to cause chain transfer reaction by the addition of hydrogen, and as a result, terminal groups of the polymer are saturated (for example, Patent Documents 6 and 7).

Therefore, to obtain a polymer having unsaturated double bonds in a high ratio, the addition of hydrogen was considered to be avoided.

Patent Document 1: Japanese Examined Patent Publication No. H07-116065
Patent Document 2: Japanese Patent No. 3073234
Patent Document 3: Japanese Publication of Translation of PCT No. 2002-518528
Patent Document 4: Japanese Publication of Translation of PCT No. 2002-522572
Patent Document 5: Japanese Publication of Translation of PCT No. 2002-522575
Patent Document 6: Japanese Patent No. 3058419
Patent Document 7: Japanese Patent No. 3086469

DISCLOSURE OF THE INVENTION

The present invention is to address the above problems, and an object of the present invention is to provide a method for efficiently producing an unsaturated hydrocarbon compound having unsaturated double bonds in a high ratio, particularly a terminal vinylidene group (α-olefin dimer).

The inventors of the present invention have found that, by using an oxygen-containing organometallic compound modified with a halogen-containing compound as a component of the catalyst, an unsaturated hydrocarbon compound having unsaturated terminal double bonds in a high ratio is obtained, and thus accomplished the present invention.

The present invention was completed based on such knowledge.

Namely, the present invention provides the following:
1. A method for producing an unsaturated hydrocarbon compound, wherein an α-olefin is dimerized using a catalyst composed of a metallocene compound (A) and an oxygen-containing organometallic compound modified with a halogen-containing compound (B).
2. The method for producing an unsaturated hydrocarbon compound described in the above 1, wherein the component (B) is an oxygen-containing organometallic compound, represented by the general formula (2) and/or (3), modified with a halogen-containing compound,

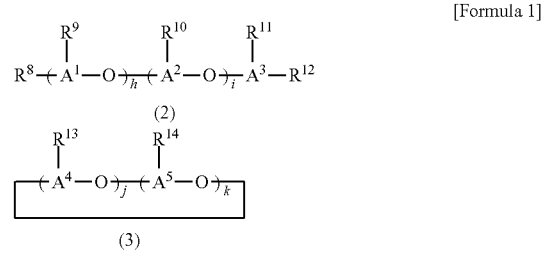

[Formula 1]

in the formula, $R^8$ to $R^{14}$ each independently represent an alkyl group having 1 to 8 carbon atoms, $A^1$ to $A^5$ each independently represent a metal element of Group 13 in the periodic table. Each of h to k is a number of 0 to 50, and both (h+i) and (j+k) are larger than 1,
3. The method for producing an unsaturated hydrocarbon compound described in the above 1 or 2, wherein the halogen-containing compound is a halogenated alkyl aluminium compound or a halogenated hydrocarbon compound,
4. The method for producing an unsaturated hydrocarbon compound described in the above 3, wherein the halogenated alkyl aluminium compound is represented by the general formula (4), $$R^{15}{}_n AlX^1{}_{3-n} \qquad (4)$$

in the formula, $R^{15}$ represents a hydrocarbyl group having 1 to 20 carbon atoms or an organometalloid group, $X^1$ represents a halogen atom, and n satisfies the relation 0<n<3.
5. The method for producing an unsaturated hydrocarbon compound described in the above 3, wherein the halogenated hydrocarbon compound is a compound in which hydrogen atoms in a hydrocarbon group having 1 to 20 carbon atoms are substituted with 1 to 4 halogen atoms,
6. The method for producing an unsaturated hydrocarbon compound described in any of the above 1 to 5, wherein the component (A) is a compound represented by the general formula (1), $$Q_a(C_5H_{5-a-b}R^1{}_b)(C_5H_{5-a-c}R^2{}_c)M^1XY \qquad (1)$$

in the formula, Q represents a connecting group for crosslinking two conjugated 5-membered ring ligands $(C_5H_{5-a-b}R^1{}_b)$ and $(C_5H_{5-a-c}R^2{}_c)$. $R^1$ and $R^2$ each represent a hydrocarbon group, a halogen atom, an alkoxy group, a silicon-containing hydrocarbon group, a phosphorus-containing hydrocarbon group, a nitrogen-containing hydrocarbon group or a boron-containing hydrocarbon group and may be the same or different from each other when plural groups are present, or may form a ring structure by bonding with each other. The symbol a is 0, 1 or 2. The symbols b and c each are an integer of 0 to 5 when a=0, an integer of 0 to 4 when a=1, and an integer of 0 to 3 when a=2. $M^1$ represents a transition metal of Group 4 in the periodic table. X and Y each represent a covalent bond ligand or an ionic bond ligand, and may be bonded with each other.

7. The method for producing an unsaturated hydrocarbon compound described in the above 6, wherein $M^1$ represents zirconium.

8. The method for producing an unsaturated hydrocarbon compound described in any of the above 1 to 7, wherein an α-olefin is dimerized in the presence of hydrogen, and 9. The method for producing an unsaturated hydrocarbon compound described in any of the above 1 to 8, wherein the ratio of unsaturated double bonds contained in the unsaturated hydrocarbon compound is 80 mol % or more.

According to the present invention, an unsaturated hydrocarbon compound having unsaturated double bonds in a high ratio, particularly a terminal vinylidene group may be economically produced in a high yield and high selectivity by using a catalyst containing a metallocene compound (A) and an oxygen-containing organometallic compound modified with a halogen-containing compound (B).

BEST MODE FOR CARRYING OUT THE INVENTION

The present invention relates to a process for producing an unsaturated hydrocarbon compound by dimerization of an α-olefin using a catalyst composed of a metallocene compound (A) and an oxygen-containing organometallic compound modified with a halogen-containing compound (B).

The following compounds may be preferably used as a component of the catalyst of the present invention.

Metallocene Compound (A)

In the present invention, although various metallocene compounds may be used, preferably a transition metal compound of Group 4 in the periodic table is used.

The transition metal compound of Group 4 in the periodic table is represented by the general formula (1),

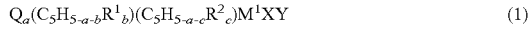

$$Q_a(C_5H_{5-a-b}R^1_b)(C_5H_{5-a-c}R^2_c)M^1XY \qquad (1)$$

where Q represents a connecting group for crosslinking two conjugated 5-membered ring ligands $(C_5H_{5-a-b}R^1_b)$ and $(C_5H_{5-a-c}R^2_c)$. $R^1$ and $R^2$ each represent a hydrocarbon group, a halogen atom, an alkoxy group, a silicon-containing hydrocarbon group, a phosphorus-containing hydrocarbon group, a nitrogen-containing hydrocarbon group or a boron-containing hydrocarbon group, and may be the same or different from each other when plural groups are present, or may form a ring structure by bonding with each other. The symbol a is 0, 1 or 2. The symbols b and c each are an integer of 0 to 5 when a=0, an integer of 0 to 4 when a=1, and an integer of 0 to 3 when a=2. $M^1$ represents a transition metal of Group 4 in the periodic table. X and Y each represent a covalent bond ligand or an ionic bond ligand, and may be bonded with each other.

Specific examples of Q include:

(1) Alkylene group having 1 to 20 carbon atoms such as methylene group, ethylene group, propylene group, butylene group, isopropylene group, methylphenyl methylene group, diphenyl methylene group, cyclohexylene group and the like, cycloalkylene group, or cycloalkylene group having side chain lower alkyl or phenyl-substituted cycloalkylene group.

(2) Silylene group such as silylene group, dimethylsilylene group, methylphenyl silylene group, diphenylsilylene group, disilylene group, tetramethyldisilylene group and the like, oligo silylene group, or oligo silylene group having side chain lower alkyl or phenyl-substituted oligo silylene group.

(3) Hydrocarbon containing germanium, phosphorus, nitrogen, boron or aluminum group [lower alkyl group, phenyl group, hydrocarbyloxy group (preferably lower alkoxy group) and the like] such as $(CH_3)_2Ge$ group, $(C_6H_5)_2Ge$ group, $(CH_3)P$ group, $(C_6H_5)P$ group, $(C_4H_9)N$ group, $(C_6H_5)N$ group, $(CH_3)B$ group, $(C_4H_9)B$ group, $(C_6H_5)B$ group, $(C_6H_5)Al$ group, $(CH_3O)Al$ group, and the like.

Among them, alkylene group and silylene group are preferable.

Furthermore, $(C_5H_{5-a-b}R^1_b)$ and $(C_5H_{5-a-c}R^2_c)$ each represent a conjugated 5-membered ring ligand. $R^1$ and $R^2$ each represent a hydrocarbon group, a halogen atom, an alkoxy group, a silicon-containing hydrocarbon group, a phosphorus-containing hydrocarbon group, a nitrogen-containing hydrocarbon group or a boron-containing hydrocarbon group. The symbol a is 0, 1 or 2.

The symbols b and c each are an integer of 0 to 5 when a=0, an integer of 0 to 4 when a=1, and an integer of 0 to 3 when a=2.

As the hydrocarbon group mentioned above, those having 1 to 20 carbon atoms are preferable, and those having 1 to 12 carbon atoms are particularly preferable.

The hydrocarbon group as a monovalent group, may be bonded to a cyclopentadienyl group that is a conjugated 5-membered ring group, or when plural groups are present, two of them may be bonded with each other to form a ring structure together with a part of cyclopentadienyl group.

Namely, representative examples of conjugated 5-membered ring ligand include substituted or unsubstituted cyclopentadienyl group, indenyl group and fluorenyl group.

As the halogen atom, chlorine, bromine, iodine and fluorine atoms are cited, and as alkoxy group, those having 1 to 12 carbon atoms are cited preferably.

Examples of silicon-containing hydrocarbon group include —Si $(R^3)(R^4)(R^5)$ (where $R^3$, $R^4$ and $R^5$ each represent a hydrocarbon group having 1 to 24 carbon atoms) and the like, examples of the phosphorous-containing hydrocarbon group, nitrogen-containing hydrocarbon group and boron-containing hydrocarbon group include, respectively, —P$(R^6)(R^7)$, —N$(R^6)(R^7)$, —B$(R^6)(R^7)$ and the like, where $R^6$ and $R^7$ each represent a hydrocarbon group having 1 to 18 carbon atoms.

When plural $R^1$s and $R^2$s are present, they may be the same or different from each other.

Furthermore, in a compound represented by the general formula (1), conjugated 5-membered ring ligands $(C_5H_{5-a-b}R^1_b)$ and $(C_5H_{5-a-c}R^2_c)$ may be the same or different from each other.

$M^1$ represents a transition metal element of Group 4 in the periodic table, and specific examples include titanium, zirconium, hafnium, of which zirconium is most preferable.

X and Y each represent a covalent bonding ligand or an ionic bonding ligand. Specific examples include hydrogen atom, halogen atom, hydrocarbon group having 1 to 20 carbon atoms, preferably 1 to 10 carbon atoms, alkoxy group having 1 to 20 carbon atoms, preferably 1 to 10 carbon atoms, amino group, a phosphorous-containing hydrocarbon group having 1 to 20 carbon atoms, preferably 1 to 12 carbon atoms (such as diphenyl phosphine group) or silicon-containing hydrocarbon group having 1 to 20 carbon atoms, preferably 1 to 12 carbon atoms (such as trimethylsilyl group), hydrocarbon group having 1 to 20 carbon atoms, preferably 1 to 12 carbon atoms, or halogen-containing boron compound (such as $B(C_6H_5)_4$, $BF_4$).

Among those groups, hydrogen atom, halogen atom, hydrocarbon group and alkoxy group are preferable.

X and Y may be the same or different from each other.

Specific examples of a compound represented by the above general formula (1) include compounds described in the following (a) to (f):

(a) Transition metal compound having two conjugated 5-membered ring ligands without having a crosslinking bonding group, such as bis(cyclopentadienyl)zirconium dichloride, bis(methylcyclopentadienyl)zirconium dichloride, bis(1,3-dimethylcyclopentadienyl)zirconium dichloride, bis(1,2,4-trimethylcyclopentadienyl)zirconium dichloride, bis(tetramethylcyclopentadienyl)zirconium dichloride, bis(pentamethyl cyclopentadienyl)zirconium dichloride, bis(n-butylcyclopentadienyl)zirconium dichloride, bis(trimethylsilylcyclopentadienyl)zirconium dichloride, bis[bis(trimethylsilyl)cyclopentadienyl]zirconium dichloride, bis(trimethylsilyl methyl cyclopentadienyl)zirconium dichloride, bis(indenyl)zirconium dichloride, bis(1,2,3-trimethylindenyl)zirconium dichloride, bis(1,2,3-trimethyl tetrahydro indenyl)zirconium dichloride, bis(fluorenyl)zirconium dichloride, bis(9-methylfluorenyl)zirconium dichloride, bis(9-methyloctahydrofluorenyl)zirconium dichloride, bis(cyclopentadienyl)zirconium chlorohydride, bis(cyclopentadienyl)methyl zirconium chloride, bis(cyclopentadienyl)ethyl zirconium chloride, bis(cyclopentadienyl) methoxy zirconium chloride, bis(cyclopentadienyl)phenyl zirconium chloride, bis(cyclopentadienyl)dimethyl zirconium, bis(cyclopentadienyl)diphenyl zirconium, bis(cyclopentadienyl)dineopentyl zirconium, bis(cyclopentadienyl)dihydrozirconium, bis(cyclopentadienyl)dimethoxyzirconium, (cyclopentadienyl)(pentamethylcyclopentadienyl)zirconium dichloride, (cyclopentadienyl)(indenyl)zirconium dichloride, (cyclopentadienyl)(fluorenyl)zirconium dichloride, and the like, (b) Transition metal compound having two conjugated 5-membered ring ligands crosslinked by an alkylene group such as methylenebis(cyclopentadienyl)zirconium dichloride, ethylenebis(cyclopentadienyl)zirconium dichloride, 1,3-propylene bis(cyclopentadienyl)zirconium dichloride, 1,4-butylenebis(cyclopentadienyl)zirconium dichloride, isopropylidenebis(cyclopentadienyl)zirconium dichloride, rac-methylenebis(indenyl)zirconium dichloride, meso-methylenebis(indenyl)zirconium dichloride, rac-ethylenebis(indenyl)zirconium dichloride, meso-ethylene bis(indenyl)zirconium dichloride, ethylenebis(fluorenyl)zirconium dichloride, rac-1,3-propylenebis(indenyl)zirconium dichloride, meso-1,3-propylene bis(indenyl)zirconium dichloride, rac-1,4-butylenebis(indenyl)zirconium dichloride, meso-1,4-butylenebis(indenyl)zirconium dichloride, rac-ethylene bis(4,5,6,7-tetrahydro indenyl)zirconium dichloride, meso-ethylene bis(4,5,6,7-tetrahydro indenyl)zirconium dichloride, rac-ethylenebis(2-methylindenyl)zirconium dichloride, meso-ethylene bis(2-methylindenyl)zirconium dichloride, rac-ethylenebis(2,3-dimethylindenyl)zirconium dichloride, meso-ethylenebis(2,3-dimethylindenyl)zirconium dichloride, ethylene(2,4-dimethylcyclopentadienyl)(3',5'-dimethyl cyclopentadienyl)zirconium dichloride, ethylene(2-methyl-4-tert-butylcyclopentadienyl)(3'-tert-butyl-5'-methyl cyclopentadienyl)zirconium dichloride, ethylene(2,3,5-trimethyl cyclopentadienyl) (2',4',5'-trimethylcyclopentadienyl)zirconium dichloride, ethylene bis(tetramethyl cyclopentadienyl) zirconium dichloride, methylene(cyclopentadienyl)(3,4-dimethyl cyclopentadienyl)zirconium dichloride, methylene (cyclopentadienyl)(trimethyl cyclopentadienyl)zirconium dichloride, methylene(cyclopentadienyl)(tetramethyl cyclopentadienyl)zirconium dichloride, isopropylidene(cyclopentadienyl) (3,4-dimethylcyclopentadienyl)zirconium dichloride, isopropylidene(cyclopentadienyl)(tetramethylcyclopentadienyl)zirconium dichloride, isopropylidene(cyclopentadienyl) (3-methylindenyl)zirconium dichloride, isopropylidene(cyclopentadienyl)(fluorenyl)zirconium dichloride, isopropylidene(2-methylcyclopentadienyl)(fluorenyl)zirconium dichloride, isopropylidene(2,5-dimethylcyclopentadienyl)(3,4-dimethylcyclopentadienyl)zirconium dichloride, isopropylidene(2,5-dimethylcyclopentadienyl)(fluorenyl) zirconium dichloride, ethylene(cyclopentadienyl)(2,4-dimethylcyclopentadienyl)zirconium dichloride, ethylene(cyclopentadienyl)(fluorenyl)zirconium dichloride, ethylene (2,5-dimethyl cyclopentadienyl)(fluorenyl)zirconium dichloride, ethylene(2,5-diethyl cyclopentadienyl)(fluorenyl)zirconium dichloride, diphenylmethylene (cyclopentadienyl)(3,4-diethylcyclopentadienyl)zirconium dichloride, diphenyl methylene(cyclopentadienyl)(3,4-diethylcyclopentadienyl)zirconium dichloride, cyclohexylidene(cyclopentadienyl)(fluorenyl)zirconium dichloride, cyclohexylidene (2,5-dimethylcyclopentadienyl)(3',4'-dimethylcyclopentadienyl) zirconium dichloride, and the like, (c) Transition metal compound having two conjugated 5-membered ring ligands crosslinked by a silylene group such as dimethylsilylene bis(cyclopentadienyl)zirconium dichloride, phenylmethylsilylene bis(cyclopentadienyl)zirconium dichloride, diphenylsilylene bis(cyclopentadienyl) zirconium dichloride, tetramethyl disilylene bis(cyclopentadienyl)zirconium dichloride, dimethyl silylene (cyclopentadienyl) (tetramethylcyclopentadienyl)zirconium dichloride, and the like, (d) Transition metal compound having two conjugated 5-membered ring ligands which are crosslinked by a hydrocarbon group containing germanium, aluminum, boron, phosphorous or nitrogen such as dimethylgermylenebis(cyclopentadienyl)zirconium dichloride, methylalumilenebis (cyclopentadienyl)zirconium dichloride, phenylalumilenebis (cyclopentadienyl)zirconium dichloride, phenylphosphilene bis(cyclopentadienyl)zirconium dichloride, ethylborenebis (cyclopentadienyl)zirconium dichloride, phenylamylenebis (cyclopentadienyl)zirconium chloride, and the like.

(e) Transition metal compound having two conjugated 5-membered ring ligands doubly crosslinked with each other such as (1,1'-dimethylsilylene)(2,2'-isopropylidene) bis(cyclopentadienyl)zirconium dichloride, (1,1'-ethylene)(2,2'-ethylene) bis(cyclopentadienyl)zirconium dichloride, (1,1'-dimethylsilylene)(2,2'-dimethylsilylene)bis(cyclopentadienyl)zirconium dichloride, (1,2'-dimethylsilylene)(2,1'-ethylene)bis(indenyl)zirconium dichloride, (1,1'-dimethylsilylene)(2,2'-ethylene)bis(indenyl)zirconium dichloride, (1,1'-ethylene) (2,2'-dimethylsilylene)bis(indenyl)zirconium dichloride, (1,1'-dimethylsilylene)(2,2'-cyclohexylidene)bis(indenyl)zirconium dichloride, and the like, (f) Furthermore, a compound described in the above (a) to (e) wherein chlorine atom is replaced with bromine atom, iodine atom, hydrogen atom, methyl group, phenyl group, and the centered metal of the above compounds, zirconium, is replaced with titanium or hafnium.

(B) Oxygen-Containing Organometallic Compound Modified with a Halogen-Containing Compound The oxygen-containing organometallic compound modified with a halogen-containing compound used in the present invention is obtained by modifying the oxygen-containing organometallic compound (b1) with a halogen-containing compound (b2).

Examples of the halogen-containing compound (b2) include, as described later, a halogenated alkylaluminum compound (b3), and a halogenated hydrocarbon compound (b4).

For preparation of the component (B), the halogen-containing compound (b2), namely, the halogenated alkylaluminum compound (b3) or the halogenated hydrocarbon compound (b4) may be used alone or in a combination of two or more with the oxygen-containing organometallic compound (b1).

Oxygen-Containing Organometallic Compound (b1)

The oxygen-containing organometallic compound preferably used in the present invention is represented by the general formula (2) and/or (3):

[Formula 2]

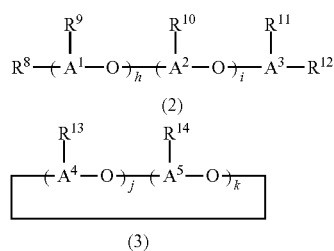

where $R^8$ to $R^{14}$ each independently represent an alkyl group having 1 to 8 carbon atoms, $A^1$ to $A^5$ each independently represent a metal element of Group 13 in the periodic table. The symbols h to k each are an integer of 0 to 50, and both (h+i) and (j+k) are larger than 1.

The alkyl groups $R^8$ to $R^{14}$ having 1 to 8 carbon atoms in the oxygen-containing organometallic compound represented by the general formula (2) and (3) include methyl group, ethyl group, n-propyl group, isopropyl group, various butyl groups, various pentyl groups, various hexyl groups, various heptyl groups, and various octyl groups. The metal elements represented by $A^1$ to $A^5$ belonging to Group 13 in the periodic table include boron, aluminum, gallium, indium, and thallium.

Among those metal elements, boron and aluminum are particularly preferable.

Further, the value of h to k is preferably in the range of 1 to 20, and particularly preferably 1 to 5.

The compounds represented by the general formulas (2) and (3) include alumoxanes such as straight chain or cyclic tetramethyl dialumoxane, tetraisobutyldialumoxane, methyl alumoxane, ethyl alumoxane, butyl alumoxane, isobutylalumoxane and the like; boroxanes such as trimethyl boroxane and methyl boroxane and the like.

Among those compounds, alumoxanes are preferable, particularly methyl alumoxane are preferable.

Halogen-Containing Compound (b2)

The halogen-containing compound used in the present invention includes halogenated alkylaluminium compound (b3) and/or halogenated hydrocarbon compound (b4).

Preferable halogenated alkylaluminum compound is represented by the general formula (4):

$$R^{15}{}_n AlX^1{}_{3-n} \quad (4)$$

where $R^{15}$ represents a hydrocarbyl group having 1 to 20 carbon atoms or an organometalloid group, $X^1$ represents a halogen atom, and n satisfies the relation 0<n<3.

Preferable examples of hydrocarbyl group and organometalloid group of $R^{15}$ in the compound represented by the general formula (4) include methyl group, ethyl group, propyl group, isopropyl group, various butyl groups, various aryl groups, various hydrocarbyl silyl group and the like.

Moreover, n in the formula is preferably 1, 1.5 or 2, more preferably 2.

Examples for n=1 include methylaluminum dichloride, ethylaluminum dichloride, n-propylaluminum dichloride, n-butylaluminum dichloride, isobutylaluminum dichloride, tert-butyl aluminum dichloride and the like.

Examples for n=1.5 include methylaluminum sesquichloride, ethylaluminum sesquichloride, n-propylaluminum sesquichloride, n-butylaluminum sesquichloride, iso-butylaluminum sesquichloride, tert-butylaluminum sesquichloride and the like.

Examples for n=2 include dimethylaluminum chloride, diethylaluminum chloride, di-n-propylaluminum chloride, di-n-butylaluminum chloride, di-isobutylaluminum chloride, di-tert-butylaluminum chloride and the like.

In the present invention, those compounds may be used alone or in a combination of two or more.

Halogenated Hydrocarbon Compound (b4)

The halogenated hydrocarbon compound used in the present invention is preferably a compound in which hydrogen atoms in a hydrocarbon group having 1 to 20 carbon atoms are substituted with 1 to 4 halogen atoms.

Preferable examples of hydrocarbon group having 1 to 20 carbon atoms include alkyl group having 1 to 20 carbon atoms, cycloalkyl group having 5 to 20 carbon atoms, aryl group having 6 to 20 carbon atoms, and aralkyl group having 7 to 20 carbon atoms.

Examples of the halogenated hydrocarbon compound include methyl chloride, ethyl chloride, propyl chloride, butyl chloride, pentyl chloride, octyl chloride, phenyl chloride, benzyl chloride, naphthyl chloride, methylene chloride, chloroform, carbon tetrachloride, methyl bromide, ethyl bromide, propyl bromide, butyl bromide, pentyl bromide, octyl bromide, phenyl bromide, benzyl bromide, naphthyl bromide, methylene bromide, bromoform, carbon tetrabromide, methyl iodide, ethyl iodide, propyl iodide, butyl iodide, pentyl iodide, octyl iodide, phenyl iodide, benzyl iodide, naphthyl iodide, methylene iodide, iodoform, carbon tetraiodide and the like.

In the present invention, those compounds may be used alone or in a combination of two or more.

Preparation of a catalyst of the present invention using the metallocene compound (A), the halogen-containing compound (b2) and the oxygen-containing organometallic compound (b1) is preferably conducted under atmosphere of an inert gas such as nitrogen.

In the preparation of the oxygen-containing organometallic compound (b1) modified with the halogen-containing compound (b2), (B), modification reaction of the oxygen-containing organometallic compound (b1) by the halogen-containing compound (b2) may be conducted by contacting the component (b1) and the component (b2) in advance, but, as the modification reaction proceeds quickly, a catalyst having sufficiently high activity can be obtained by contacting the component (b1) and the component (b2) in the presence of an α-olefin.

The catalyst components prepared in advance in a catalyst preparation vessel may be used, or alternatively, the catalyst components prepared in a reactor used for the dimerization reaction of the α-olefin may be also used for the reaction.

When the catalyst is prepared in a reactor, temperature is preferably adjusted to be lower than the temperature for dimerization reaction of the α-olefin, for example, in the range of −30 to 200° C., preferably 0 to 150° C.

In the dimerization reaction of the present invention, presence of hydrogen increases the yield of the desired unsaturated hydrocarbon compound.

Hydrogen may be introduced into the component (A), the component (b1) and the component (b2) from the beginning without using an inert gas such as nitrogen, or alternatively, may be introduced after the component (A), the component (b1) and the component (b2) are mixed and contacted with α-olefin.

The mixing ratio of the oxygen-containing organometallic compound (b1) to the halogenated alkylaluminum compound (b3), in terms of component (b1)/component (b3) [molar ratio] is normally 0.01 to 10 equivalent, preferably 0.05 to 5 equivalent and more preferably 0.1 to 3 equivalent per metal atom.

If the above ratio is smaller than 0.01 equivalent, the catalyst activity may decrease, if larger than 10 equivalent, a saturated dimer of the α-olefin may be formed, and the ratio of the desired unsaturated groups in the unsaturated hydrocarbon compound may decrease, or the yield may decrease.

The mixing ratio of the oxygen-containing organometallic compound (b1) to the halogenated hydrocarbon compound (b4) in terms of component (b1)/component (b4) [molar ratio] is normally 0.01 to 20 equivalent, preferably 0.05 to 10 equivalent and more preferably 0.1 to 5 equivalent per metal atom.

If the above ratio is smaller than 0.01 equivalent, the catalyst activity may decrease, if the ratio exceeds 20 equivalent, the yield of the desired unsaturated hydrocarbon compound may decrease.

Further, in the case where the component (b1) is modified by the component (b3) and the component (b4), the mixing ratio in terms of the component (b1)/[components (b3)+(b4)] (molar ratio) is normally 0.01 to 20 equivalent, preferably 0.05 to 10 equivalent, and more preferably 0.1 to 5 equivalent per metal atom.

The mixing ratio of the transition metal compound (A) to the oxygen-containing organometallic compound (b1) in terms of the component (A)/the component (b1) [molar ratio] is normally 1/1 to 1/1000 and preferably 1/2 to 1/100.

If the above ratio is smaller than 1/1, the catalyst activity may not be realized, if the ratio exceeds 1/1000, a high molecular weight polymer of the α-olefin may be formed, and the yield of the desired unsaturated hydrocarbon compound may decrease, or a saturated dimer of the α-olefin may be formed, and the ratio of unsaturated groups in the unsaturated hydrocarbon compound may decrease.

The mixing ratio of the transition metal compound (A) to the halogenated alkylaluminum compound (b3) in terms of the component (A)/the component (b3) [molar ratio] is normally 1/0.5 to 1/100, preferably 1/1 to 1/20, and the mixing ratio of the transition metal compound (A) to the halogenated hydrocarbon compound (b4) in terms of the component (A)/the component (b4) [molar ratio] is normally 1/0.5 to 1/200, and preferably 1/1 to 1/50.

Furthermore, when the component (b1) is modified by the component (b3) and the component (b4), the mixing ratio to the component (A) in terms of the component (A)/[components (b3)+(b4)] (molar ratio) is normally 1/0.5 to 1/200 and preferably 1/1 to 1/50.

The amount of added hydrogen is normally 0.1 to 700 kPa, and preferably 0.5 to 100 kPa.

Namely, the molar ratio of hydrogen to the metallocene compound (A) is normally 1/1 to 10000/1, preferably 1/1 to 1000/1, and more preferably 5/1 to 1000/1.

Moreover, the molar ratio of hydrogen to the α-olefin is normally 1/10000 to 1/1, preferably 1/10000 to 1/10, and more preferably 1/2000 to 1/10.

If the amount of added hydrogen is excessive, a saturated dimer of the α-olefin may be formed, and the ratio of unsaturated groups in the unsaturated hydrocarbon compound may decrease.

Although the α-olefin used in the present invention is not particularly limited, examples of preferable α-olefin include propylene, 1-butene, 3-methyl-1-butene, 4-methyl-1-butene, 4-phenyl-1-butene, 1-pentene, 3-methyl-1-pentene, 4-methyl-1-pentene, 3,3-dimethyl-1-pentene, 3,4-dimethyl-1-pentene, 4,4-dimethyl-1-pentene, 1-hexene, 4-methyl-1-hexene, 5-methyl-1-hexene, 6-phenyl-1-hexene, 1-octene, 1-decene, 1-dodecene, 1-tetradecene, 1-hexadecene, 1-octadecene, 1-eicocene, 1-dococene, 1-tetracocene, 1-hexacocene, 1-octacocene, 1-triacontene, 1-doriacontene, 1-tetracontene, vinylcyclohexane and the like.

In the present invention, the above α-olefins may be used alone or in a combination of two or more.

The unsaturated hydrocarbon compound obtained in the present invention contains normally 80 mol % or more of the unsaturated double bond, particularly the ratio of the terminal vinylidene group is normally 75 mol % or more.

In the present invention, the method for reaction is not limited, and the reaction may be conducted in the absence of a solvent or in the presence of a solvent, and either method may be employed.

With respect to the reaction conditions, the reaction temperature is −100 to 250° C., particularly −50 to 100° C. is preferable.

The ratio of the amount of catalyst to α-olefin in terms of the α-olefin/the metallocene compound (A) (molar ratio) is normally 1000 to $10^6$, and preferably 2000 to $10^5$.

The reaction time is normally 10 minutes to 48 hours.

If a solvent is used in the reaction, examples of the solvent include aromatic hydrocarbon such as benzene, toluene, xylene, ethylbenzene and the like, alicyclic hydrocarbon such as cyclopentane, cyclohexane, methyl cyclohexane and the like, aliphatic hydrocarbon such as pentane, hexane, heptane, octane and the like, halogenated hydrocarbon such as chloroform, dichloromethane and the like.

The above solvent may be used alone or in a combination of two or more.

Moreover, the raw material such as the α-olefin may be used as a solvent.

EXAMPLES

The present invention is explained in further detail with reference to examples. However, the present invention is by no means restricted by these examples.

Reference Example 1

In a glass container having a 100 mL internal volume, 1.0 ml of a deuterated benzene ($C_6D_6$) solution of methylaluminoxane (MAO) adjusted to 1.0 mol/L was charged at 25° C.

Then, 1.0 ml of a deuterated benzene ($C_6D_6$) solution of diethylaluminum chloride (DEAC) adjusted to 1.0 mol/L was added to the above solution and the resultant solution was stirred for 10 minutes.

Subsequently, 1.0 mL of a deuterated benzene ($C_6D_6$) solution of bis(cyclopentadienyl)zirconium dichloride (Cp$_2$ZrCl$_2$) adjusted to 0.1 mol/L was added and stirred. The result of $^1$H-NMR measurement of this catalyst system is shown in Table 1.
[Table 1]

Subsequently, when the 0.1 volume % toluene solution of benzalacetophenone was added to this solution, the color turned yellow.

TABLE 1

| Catalyst system (mol ratio) | | Peak due to promoter | | Peak due to catalyst + promoter | | | |
|---|---|---|---|---|---|---|---|
| | | | | near Zr—H | | near C$_5$H$_5$ | |
| Catalyst | Promoter | Chemical shift (ppm) | Assigned to | Chemical shift | Assigned to | Chemical shift | Assigned to |
| Cp$_2$ZrCl$_2$ (1) | MAO + DEAC (10) + (10) reaction product | −0.27<br>−0.2~0.0 (br)<br>0.18<br>1.10 | (CH$_3$)$_3$Al<br>—((CH$_3$)Al)O)—<br>AlCH$_2$CH$_3$<br>AlCH$_2$CH$_3$ | 0.8<br>0.8 | Zr—H<br>Al—H | 5.35 | C$_5$H$_5$ |
| Cp$_2$ZrCl$_2$ (1) | MAO (10) | −0.37<br>−0.6~−0.1 (br) | (CH$_3$)$_3$Al<br>—((CH$_3$)Al)O)— | 0.45 | Zr—CH$_3$ | 5.70 | C$_5$H$_5$ |
| Cp$_2$ZrCl$_2$ (1) | DEAC (10) | 0.25<br>1.15 | AlCH$_2$CH$_3$<br>AlCH$_2$CH$_3$ | 0.8 | Zr—H | 5.88 | C$_5$H$_5$ |

From Table 1, it was confirmed that the catalyst system of the present invention is not a simple mixture of the product from the reaction of bis(cyclopentadienyl)zirconium dichloride (A) with methylaluminoxane (b1) and the product from the reaction of bis(cyclopentadienyl)zirconium dichloride (A) with diethylaluminum chloride (b3).

Furthermore, 18 mL of toluene and 1.0 mL of a toluene solution of methylaluminoxane adjusted to 1.0 mol/L were charged to a glass container having a 100 mL internal volume at 25° C.

Then, 0.5 mL of a toluene solution of diethyl aluminumchloride adjusted to 1.0 mL/L was added to above solution, and the resultant solution was heated up to 50° C., and stirred for 5 minutes.

Subsequently, the solution was cooled down to 25° C., and the solvent was distilled off under 13.33 Pa and subjected to vacuum drying. After hours, there was no further weight decrease observed, and 0.74 g of white powder was obtained.

As the result of an elemental analysis of the above white powder, 5.2 weight % of chlorine was detected, by which it was confirmed that methylaluminoxane was modified by diethylaluminum chloride.

Moreover, measurement of the acid strength (acidity) distribution of the modified methylaluminoxane (B) obtained above was made. The results are shown in Table 2.
[Measurement Of Acid Strength Distribution]

Measurement of the acid strength distribution was made according to the following method completely in nitrogen atmosphere.

A 0.1 volume % toluene solution for each of nitrobenzene, benzalacetophenone, dicinnamalacetone, and a 0.1 mol/L toluene solution for each of methylaminoxane, diethylaluminum chloride and butylamine were prepared, respectively.
(Measurement of the Acid Strength Distribution of Methylaluminoxane)

In a conical flask was charged 5.0 mL of a 0.1 mol/L toluene solution of methylaluminoxane mentioned above. When 0.1 mL of the above 0.1 volume % toluene solution of nitrobenzene was added to the solution, the color of the solution turned yellow.

From a burette, the 0.1 mol/L toluene solution of butylamine was added dropwise to determine the acid strength in the range of pKa of −12.1 and lower from the amount of solution added until an endpoint at color change.

The acid strength in the range of pKa of −12.1 to −5.0 was determined by the amount of the butylamine solution added from a burette until an endpoint of color change.

Subsequently, when 0.1 mL of the 0.1 volume % toluene solution of dicinnamalacetone was added to this solution, the color turned red.

The acid strength in the range of pKa of −5.6 to −3.0 was determined by the amount of the butylamine solution added from a burette until an endpoint of color change.

The results are shown in Table 2.
(Measurement of the Acid Strength Distribution of Modified Methylaluminoxane)

In a conical flask were charged 5.0 mL of the above 0.1 mol/L toluene solution of methylaluminoxane, and 2.5 mL of the 0.1 mol/L toluene solution of diethylaluminum chloride and the resultant solution was stirred for 10 minutes to prepare a toluene solution of modified methylaluminoxane (B).

The acid strength of this toluene solution of modified methylaluminoxane was measured in the same manner as in the measurement of the above methylaluminoxane.

The results are shown in Table 2.
(Measurement of the Acid Strength Distribution of Diethylaluminum Chloride)

Into a conical flask was charged 5.0 mL of the above 0.1 mol/L toluene solution of diethylaluminum chloride and the resultant solution was measured in the same manner as in the measurement of the above methylaluminoxane.
[Table 2]

TABLE 2

| | pKa | | |
|---|---|---|---|
| Promoter | ≤−12.1 (mol %) | −12.1 < ≤ −5.6 (mol %) | −5.6 < ≤ −3.0 (mol %) |
| MAO + DEAC (1) + (0.5) reaction product | 0 | 61 | 2 |
| MAO | 30 | 6 | 3 |
| DEAC | 0 | 100 | 0 |

From Table 2, it was confirmed that modified methylaluminoxane (B) of the present invention has different characteristics of the acid strength from that of methylaluminoxane (b1) or diethylaluminum chloride (b3).

Example 1

To a glass container having an internal volume of 100 mL were charged 18 mL of toluene and 0.2 mL of a toluene solution of 1.0 mol/L methylaluminoxane at 25° C.

Into this solution, 0.06 mL of a toluene solution of diethylaluminum chloride adjusted to 1.0 mol/L was added and the resultant solution was stirred for 10 minutes.

Then, 20 mL of 1-decene and 2.0 mL of a toluene solution of bis(cyclopentadienyl)zirconium dichloride adjusted to 10 mmol/L were added and the solution was heated to 50° C. while stirring, and the reaction was performed for 5 hours.

The reaction was terminated by adding dilute hydrochloric acid, and the solution obtained after decomposing and removing the catalyst was analyzed by gas chromatography. The results indicated that the conversion of raw material 1-decene was 77.6 mol %, and the yield of the dimer (unsaturated hydrocarbon compound) was 64.7 mol %.

An analysis by $^1$H-NMR indicated that the dimer contained 99.8 mol % of the unsaturated double bond (the ratio of vinylidene group was 95.7 mol %).

The results are shown in Table 3.

[Table 3]

TABLE 3

|  |  |  | Examples | | | | | | | | | |
|---|---|---|---|---|---|---|---|---|---|---|---|---|
|  |  |  | 1 | 2 | 3 | 4 | 5 | 6 | 7 | 8 | 9 |
| $Cp_2ZrCl_2$ |  | (μmol) | 20 | 20 | 20 | 20 | 20 | 20 | 20 | 20 | 20 |
| MAO |  | (μmol) | 200 | 200 | 200 | 200 | 200 | 200 | 200 | 200 | 200 |
| Halogen-containing | kind |  | DEAC | DEAC | EASC | DMAC | DIBAC | $C_4H_9Cl$ | $CH_2Cl_2$ | DEAC | DMAC |
| compound | amount | (μmol) | 60 | 200 | 10 | 40 | 40 | 100 | 200 | 60 | 40 |
| $H_2$ |  | (mL) | 0 | 0 | 0 | 0 | 0 | 0 | 0 | 0 | 0 |
| Solvent (toluene) |  | (mL) | 18 | 18 | 18 | 18 | 18 | 18 | 18 | 0 | 0 |
| Reaction temperature |  | (° C.) | 50 | 50 | 50 | 50 | 50 | 50 | 50 | 50 | 50 |
| Reaction time |  | (h) | 5 | 5 | 5 | 5 | 5 | 5 | 5 | 5 | 5 |
| Conversion |  | (%) | 77.6 | 73.9 | 70.3 | 78.4 | 77 | 66.5 | 61.9 | 91.1 | 91.2 |
| $C_{20}$ yield |  | (%) | 64.7 | 52.4 | 51.7 | 59.6 | 61.2 | 44.9 | 40.7 | 71.1 | 73.2 |
| $C_{20}$ selectivity |  | (%) | 83.4 | 70.9 | 73.5 | 76.0 | 79.5 | 67.5 | 65.8 | 78.0 | 80.3 |
| $C_{20}$ activity |  | (g $C_{20}$/h-mmol Zr) | 97.1 | 78.6 | 77.6 | 89.4 | 91.8 | 67.4 | 61.1 | 106.7 | 109.8 |
|  |  | (g $C_{20}$/h-mmol Al) | 9.7 | 7.9 | 7.8 | 8.9 | 9.2 | 6.7 | 6.1 | 10.7 | 11.0 |
| Vinylidene group ratio |  | (%) | 95.7 | 95.2 | 96.1 | 96.3 | 96.1 | 96.4 | 96 | 97.3 | 97.5 |

|  |  |  | Examples | | Comparative Examples | | | | |
|---|---|---|---|---|---|---|---|---|---|
|  |  |  | 10 | 11 | 1 | 2 | 3 | 4 | 5 |
| $Cp_2ZrCl_2$ |  | (μmol) | 20 | 20 | 20 | 20 | 20 | 20 | 20 |
| MAO |  | (μmol) | 200 | 200 | 200 | 1000 | 200 | 200 | 0 |
| Halogen-containing | kind |  | $C_4H_9Cl$ | $C_4H_9Cl$ | — | — | TIBA | TEA | DEAC |
| compound | amount | (μmol) | 100 | 100 | 0 | 0 | 2000 | 200 | 60 |
| $H_2$ |  | (mL) | 0 | 20 | 0 | 0 | 0 | 0 | 0 |
| Solvent (toluene) |  | (mL) | 0 | 0 | 18 | 18 | 18 | 18 | 18 |
| Reaction temperature |  | (° C.) | 50 | 50 | 50 | 50 | 50 | 50 | 50 |
| Reaction time |  | (h) | 5 | 5 | 5 | 5 | 5 | 5 | 5 |
| Conversion |  | (%) | 74.4 | 92.1 | 49 | 96.4 | 54.8 | 48.5 | 0 |
| $C_{20}$ yield |  | (%) | 54.6 | 77.7 | 29 | 46.5 | 11.1 | 19.9 | 0 |
| $C_{20}$ selectivity |  | (%) | 73.4 | 84.4 | 59.2 | 48.2 | 20.3 | 41.0 | — |
| $C_{20}$ activity |  | (g $C_{20}$/h-mmol Zr) | 81.9 | 116.6 | 43.5 | 69.8 | 16.7 | 29.9 | 0.0 |
|  |  | (g $C_{20}$/h-mmol Al) | 8.2 | 11.7 | 4.4 | 1.4 | 1.7 | 3.0 | 0.0 |
| Vinylidene group ratio |  | (%) | 97.3 | 97.3 | 95.3 | 95.3 | 80.2 | 94.8 | — |

DEAC: diethylaluminum chloride,
EASC: ethylaluminum sesquichloride,
DMAC: dimethylaluminum chloride,
DIBAC: diisobutylaluminum chloride

Example 2

A dimer (unsaturated hydrocarbon compound) was obtained in the same manner as in Example 1, except that the added amount of toluene solution of 1.0 mol/L diethylaluminum chloride was changed to 0.2 mL.

The results indicated that the conversion of raw material 1-decene was 73.9 mol %, and the yield of the dimer was 52.4 mol %. An analysis by $^1$H-NMR indicated that the dimer contained 99.4 mol % of the unsaturated double bond (the ratio of vinylidene group was 95.2 mol %).

The results are shown in Table 3.

Comparative Example 1

A dimer (unsaturated hydrocarbon compound) was obtained in the same manner as in Example 1, except that the toluene solution of diethyl aluminumchloride was not added. The results indicated that conversion of raw material 1-decene was 49.0 mol %, and yield of the dimer was 29.0 mol %. An analysis by $^1$H-NMR indicated that the dimer contained 99.9 mol % of the unsaturated double bond (the ratio of vinylidene group was 95.3 mol %).

The results are shown in Table 3.

Comparative Example 2

A dimer (unsaturated hydrocarbon compound) was obtained in the same manner as in Example 1, except that a toluene solution of diethylaluminum chloride was not added, but 1.0 mL of a toluene solution of methylaluminoxane adjusted to 1.0 mol/L was added.

The results indicated that the conversion of raw material 1-decene was 96.4 mol %, and the yield of the dimer was 46.5 mol %. An analysis by $^1$H-NMR indicated that the dimer contained 99.9 mol % of the unsaturated double bond (the ratio of vinylidene group was 95.3 mol %).

The results are shown in Table 3.

Comparative Example 3

A dimer (unsaturated hydrocarbon compound) was obtained in the same manner as in Example 1, except that a toluene solution of diethylaluminum chloride was not added, but 2.0 mL of a toluene solution of tri-isobutyl aluminum (TIBA) adjusted to 1.0 mol/L was added.

The results indicated that the conversion of raw material 1-decene was 54.8 mol %, and the yield of the dimer was 11.1 mol %. An analysis by $^1$H-NMR indicated that the dimer contained 84.0 mol % of the unsaturated double bond (the ratio of vinylidene group was 80.2 mol %).

The results are shown in Table 3.

Comparative Example 4

A dimer (unsaturated hydrocarbon compound) was obtained in the same manner as in Example 1, except that a toluene solution of diethylaluminum chloride was not added, but 0.2 mL of a toluene solution of triethylaluminum (TEA) adjusted to 1.0 mol/L was added.

The results indicated that the conversion of raw material 1-decene was 48.5 mol %, and the yield of the dimer was 19.9 mol %. An analysis by $^1$H-NMR indicated that the dimer contained 98.2 mol % of the unsaturated double bond (the ratio of vinylidene group was 94.8 mol %).

The results are shown in Table 3.

Comparative Example 5

Reaction was performed in the same manner as in Example 1, except that a toluene solution of methylaluminoxane was not added. Dimerization reaction did not proceed at all.

Example 3

A dimer (unsaturated hydrocarbon compound) was obtained in the same manner as in Example 1, except that, instead of a toluene solution of diethylaluminum chloride, 0.01 mL of a toluene solution of ethylaluminum sesquichloride (EASC) adjusted to 0.5 mol/L was added.

The results indicated that the conversion of raw material 1-decene was 70.3 mol %, and the yield of the dimer was 51.7 mol %. An analysis by $^1$H-NMR indicated that the dimer contained 99.9 mol % of the unsaturated double bond (the ratio of vinylidene group was 96.1 mol %).

The results are shown in Table 3.

Example 4

A dimer (unsaturated hydrocarbon compound) was obtained in the same manner as in Example 1, except that, instead of a toluene solution of diethylaluminum chloride, 0.08 mL of a toluene solution of dimethylaluminum chloride (DMAC) adjusted to 0.5 mol/L was added.

The results indicated that the conversion of raw material 1-decene was 78.4 mol %, and the yield of the dimer was 59.6 mol %. An analysis by $^1$H-NMR indicated that the dimer contained 99.9 mol % of the unsaturated double bond (the ratio of vinylidene group was 96.3 mol %).

The results are shown in Table 3.

Example 5

A dimer (unsaturated hydrocarbon compound) was obtained in the same manner as in Example 1, except that instead of toluene solution of diethyl aluminum chloride, 0.08 mL of a toluene solution of diisobutylaluminum chloride (DIBAC) adjusted to 0.5 mol/L was added.

The results indicated that the conversion of raw material 1-decene was 77.0 mol %, and the yield of the dimer was 61.2 mol %. An analysis by $^1$H-NMR indicated that the dimer contained 99.8 mol % of the unsaturated double bond (the ratio of vinylidene group was 96.1 mol %).

The results are shown in Table 3.

Example 6

A dimer (unsaturated hydrocarbon compound) was obtained in the same manner as in Example 1, except that, instead of a toluene solution of diethylaluminum chloride, 0.2 mL of a toluene solution of 1-chlorobutane ($C_4H_9Cl$) adjusted to 0.5 mol/L was added.

The results indicated that the conversion of raw material 1-decene was 66.5 mol %, and the yield of the dimer was 44.9 mol %. An analysis by $^1$H-NMR indicated that the dimer contained 99.9 mol % of the unsaturated double bond (the ratio of vinylidene group was 96.4 mol %).

The results are shown in Table 3.

Example 7

A dimer (unsaturated hydrocarbon compound) was obtained in the same manner as in Example 1, except that, instead of a toluene solution of diethylaluminum chloride, 0.4 mL of a toluene solution of methylene chloride ($CH_2Cl_2$) adjusted to 0.5 mol/L was added.

The results indicated that the conversion of raw material 1-decene was 61.9 mol %, and the yield of the dimer was 40.7 mol %. An analysis by $^1$H-NMR indicated that the dimer contained 99.9 mol % of the unsaturated double bond (the ratio of vinylidene group was 96.0 mol %).

The results are shown in Table 3.

Example 8

In a glass container having an internal volume of 100 mL, were charged 20 mL of 1-decene and 0.2 mL of a toluene solution of 1.0 mol/L methylaluminoxane at 25° C.

Into this solution, 0.06 mL of a toluene solution of diethylaluminum chloride adjusted to 1.0 mol/L was added and the resultant solution was stirred for 10 minutes.

Subsequently, 2.0 mL of a toluene solution of bis(cyclopentadienyl)zirconium dichloride adjusted to 10 mmol/L was added and the solution was heated to 50° C. while stirring, and the reaction was performed for 5 hours.

The reaction was terminated by adding dilute hydrochloric acid, and the solution obtained after decomposing and removing the catalyst was analyzed by gas chromatography. The results indicated that the conversion of raw material 1-decene was 91.1 mol %, and the yield of the dimer was 71.1 mol %.

An analysis by $^1$H-NMR indicated that the dimer contained 99.7 mol % of the unsaturated double bond (the ratio of vinylidene group was 97.3 mol %).

The results are shown in Table 3.

Example 9

A dimer (unsaturated hydrocarbon compound) was obtained in the same manner as in Example 8, except that, instead of a toluene solution of diethylaluminum chloride, 0.08 mL of a toluene solution of dimethylaluminum chloride adjusted to 0.5 mol/L was added.

The results indicated that the conversion of raw material 1-decene was 91.2 mol %, and the yield of the dimer was 73.2 mol %. An analysis by $^1$H-NMR indicated that the dimer contained 99.9 mol % of the unsaturated double bond (the ratio of vinylidene group was 97.5 mol %).

The results are shown in Table 3.

Example 10

A dimer (unsaturated hydrocarbon compound) was obtained in the same manner as in Example 8, except that, instead of a toluene solution of diethylaluminum chloride, 0.2 mL of a toluene solution of 1-chlorobutane adjusted to 0.5 mol/L was added.

The results indicated that the conversion of raw material 1-decene was 74.4 mol %, and the yield of the dimer was 54.6 mol %. An analysis by $^1$H-NMR indicated that the dimer contained 99.9 mol % of the unsaturated double bond (the ratio of vinylidene group was 97.3 mol %).

The results are shown in Table 3.

Example 11

A dimer (unsaturated hydrocarbon compound) was obtained in the same manner as in Example 8, except that, instead of a toluene solution of diethylaluminum chloride, 0.2 mL of a toluene solution of 1-chlorobutane adjusted to 0.5 mol/L was added, and 20 mL (0.1 MPa) of hydrogen was introduced.

The results indicated that the conversion of raw material 1-decene was 92.1 mol %, and the yield of the dimer was 77.7 mol %. An analysis by $^1$H-NMR indicated that the dimer contained 99.7 mol % of the unsaturated double bond (the ratio of vinylidene group was 97.3 mol %).

The results are shown in Table 3.

Example 12

To a glass container having an internal volume of 100 mL, were charged 20 mL of 1-decene and 0.1 mL of a toluene solution of 1.0 mol/L methylaluminoxane at 25° C.

Into this solution, 0.03 mL of a toluene solution of diethylaluminum chloride adjusted to 1.0 mol/L was added and the resultant solution was stirred for 10 minutes.

Then, 2.0 mL of a toluene solution of dimethylsilylenebis(cyclopentadienyl)zirconium dichloride adjusted to 10 mmol/L was added and the solution was heated to 50° C. while stirring, ant the reaction was performed for 5 hours.

The reaction was terminated by adding dilute hydrochloric acid, and the solution obtained after decomposing and removing the catalyst was analyzed by gas chromatography. The results indicated that the conversion of raw material 1'-decene was 53.8 mol %, and the yield of the dimer (unsaturated hydrocarbon compound) was 45.9 mol %.

An analysis by $^1$H-NMR indicated that the dimer contained 99.5 mol % of the unsaturated double bond (the ratio of vinylidene group was 96.8 mol %).

The results are shown in Table 4.

[Table 4]

TABLE 4

|  |  | Example 12 | Comparative Example 6 |
|---|---|---|---|
| Catalyst (a) | (μmol) | 10 | 10 |
| MAO | (μmol) | 100 | 100 |
| Halogen-containing compound | kind | DEAC | — |
|  | amount (μmol) | 30 | 0 |
| $H_2$ | (mL) | 0 | 0 |
| Solvent (toluene) | (mL) | 0 | 0 |
| Reaction temperature | (° C.) | 50 | 50 |
| Reaction time | (h) | 5 | 5 |
| Conversion | (%) | 53.8 | 54.3 |
| C20 yield | (%) | 45.9 | 34.9 |
| C20 selectivity | (%) | 85.3 | 64.3 |
| C20 activity | (g C20/h-mmol Zr) | 137.7 | 104.7 |
|  | (g C20/h-mmol Al) | 13.8 | 10.5 |
| Vinylidene group ratio | (%) | 96.8 | 96.3 |

(a): dimethylsilylenebis(cyclopentadienyl)zirconium dichloride

Comparative Example 6

A dimer (unsaturated hydrocarbon compound) was obtained in the same manner as in Example 12, except that a toluene solution of 1.0 mol/L diethylaluminum chloride was not added.

The results indicated that the conversion of raw material 1-decene was 54.3 mol %, and the yield of the dimer was 34.9 mol %. An analysis by $^1$H-NMR indicated that the dimer contained 99.2 mol % of the unsaturated double bond (the ratio of vinylidene group was 96.3 mol %).

The results are shown in Table 4.

Example 13

Synthesis of Modified Methylaluminoxane

To a glass container having a 100 mL internal volume were charged 1.0 mL of a toluene solution of methylaluminoxane adjusted to 1.0 mol/L and 0.5 mL of a toluene solution of diethylaluminum chloride adjusted to 1.0 mol/L at 25° C., and the resultant solution was heated up to 50° C. and stirred for 5 hours.

Subsequently, the solution was cooled down to 25° C., and the solvent was distilled off under 13.33 Pa and subjected to vacuum drying. After 8 hours of drying, there was no further weight decrease observed, and 0.74 g of white powder (A) was obtained.

As the result of an elemental analysis of the above white powder, 5.2 weight % of chlorine was detected, by which it was confirmed that MAO was modified by DEAC.

(Dimerization Reaction)

In a glass container having an internal volume of 100 mL were charged at 25° C. 20 mL of 1-decene and 1 mL of a toluene suspension prepared by adding 0.353 g of the above white powder (A) to 22.1 mL of toluene. Further, into this mixture, 2.0 mL of a toluene solution of bis(cyclopentadienyl)zirconium dichloride adjusted to 10 mmol/L was added, the resultant mixture was heated to 50° C., and the reaction was performed for 5 hours.

The reaction was terminated by adding dilute hydrochloric acid, and the solution obtained after decomposing and removing the catalyst was analyzed by gas chromatography. The results indicated that the conversion of raw material 1-decene was 69.1 mol %, and the yield of the dimer was 61.8 mol %.

An analysis by $^1$H-NMR indicated that the dimer contained 99.6 mol % of the unsaturated double bond (the ratio of vinylidene group was 97.6 mol %).

The results are shown in Table 5.

[Table 5]

Comparative Example 7

Synthesis of Dry Methylaluminoxane

To a glass container having a 100 mL internal volume was charged 1.0 mL of a toluene solution of methylaluminoxane adjusted to 1.0 mol/L at 25° C., and the solution was heated up to 50° C. and stirred for 5 hours.

Subsequently, the solution was cooled back to 25° C., and the solvent was distilled off under 13.33 Pa and subjected to vacuum drying. After 8 hours of drying, there was no further weight decrease observed and 0.54 g of white powder (B) was obtained.

(Dimerization Reaction)

In a glass container having an internal volume of 100 mL were charged at 25° C. 20 mL of 1-decene and 1 mL of a toluene suspension prepared by adding 0.540 g of the above white powder (B) in 46.6 mL of toluene. Further, into this solution, 2.0 mL of a toluene solution of bis(cyclopentadienyl)zirconium dichloride adjusted to 10 mmol/L was added and the solution was heated up to 50° C. while stirring, and the reaction was performed for 5 hours.

The reaction was terminated by adding dilute hydrochloric acid, and the solution obtained after decomposing and removing the catalyst was analyzed by gas chromatography. The results indicated that the conversion of raw material 1-decene was 49.6 mol %, and the yield of the dimer was 40.3 mol %.

An analysis by $^1$H-NMR indicated that the dimer contained 99.5 mol % of the unsaturated double bond (the ratio of vinylidene group was 97.2 mol %).

The results are shown in Table 5.

Example 14

In a glass container having an internal volume of 100 mL were charged at 25° C. 20 mL of 1-decene, 1 mL of a toluene solution of 0.2 mol/L methylaluminoxane, 1.0 mL of a toluene solution of 1.0 mol/L diethylaluminum chloride, 2.0 mL of a toluene solution of bis(cyclopentadineyl)zirconium dichloride adjusted to 10 mmol/L, and the resultant solution was heated to 50° C. while stirring, and the reaction was performed for hours.

The reaction was terminated by adding dilute hydrochloric acid, and the solution obtained after decomposing and remov-

TABLE 5

|  |  | Example 13 | Comparative Example 7 | Example 14 | Comparative Example 8 |
|---|---|---|---|---|---|
| $Cp_2ZrCl_2$ | (µmol) | 20 | 20 | 20 | 20 |
| Promoter kind | | MAO + DEAC dried solid reaction product | MAO dried solid | MAO + DEAC reaction product | Untreated MAO |
| amount | (µmol) | 200 | 200 | 200 (MAO) + 10 (DEAC) | 200 |
| $H_2$ | (mL) | 0 | 0 | 0 | 0 |
| Solvent (toluene) | (mL) | 0 | 0 | 0 | 0 |
| Reaction temperature | (° C.) | 50 | 50 | 50 | 50 |
| Reaction time | (h) | 5 | 5 | 5 | 5 |
| Conversion | (%) | 69.1 | 49.6 | 78.2 | 55.2 |
| $C_{20}$ yield | (%) | 61.8 | 40.3 | 69.1 | 45.7 |
| $C_{20}$ selectivity | (%) | 89.4 | 81.3 | 88.4 | 82.8 |
| $C_{20}$ activity | (g $C_{20}$/h-mmolZr) | 92.7 | 60.5 | 103.7 | 68.6 |
| | (g $C_{20}$/h-mmolAl) | 9.3 | 6.0 | 20.7 | 6.9 |
| Vinylidene group ratio | (%) | 97.6 | 97.2 | 97.3 | 96.9 | ing the catalyst was analyzed by gas chromatography. The results indicated that the conversion of raw material 1-decene was 78.2 mol %, and the yield of the dimer was 69.1 mol %.

An analysis by $^1$H-NMR indicated that the dimer contained 99.2 mol % of the unsaturated double bond (the ratio of vinylidene group was 97.3 mol %).

The results are shown in Table 5.

Comparative Example 8

A dimer (unsaturated hydrocarbon compound) was obtained in the same manner as in Example 14, except that a toluene solution of 1.0 mol/L diethylaluminum chloride was not added.
The results indicated that the conversion of raw material 1-decene was 55.2 mol %, and the yield of the dimer was 45.7 mol %. An analysis by $^1$H-NMR indicated that the dimer contained 99.4 mol % of the unsaturated double bond (the ratio of vinylidene group was 96.9 mol %).

The results are shown in Table 5.

Example 15

In a glass container having an internal volume of 1 L were charged 20 mL of toluene and 8 mL of a toluene solution of methylaluminoxane adjusted to 1.0 mol/L at 25° C.

Into this solution, 1.5 mL of a toluene solution of 1.0 mol/L diethylaluminum chloride was charged and the resultant solution was stirred for 10 minutes.

Subsequently, 466 mL of 1-octene and 50 mL of a toluene solution of bis(cyclopentadienyl)zirconium dichloride were added to the solution at 25° C., the resultant solution was heated up to 45° C., and subjected to reaction.

A 1 mL sample of the reaction solution was taken at a certain interval of time, and the reaction in each sample was terminated by adding dilute hydrochloric acid, and a solution obtained after decomposing and removing the catalyst was analyzed by gas chromatography for each sample.

The results indicated that, after 2 hours of reaction, the conversion of raw material 1-octene was 56.9 mol %, and the yield of the dimer was 54.2 mol %. After 8 hours of reaction, the conversion of raw material 1-octene was 96.8 mol % and the yield of the dimer was 92.7 mol %.

An analysis by $^1$H-NMR indicated that the dimer contained 99.7 mol % of the unsaturated double bond (the ratio of vinylidene group was 95.8 mol %).

The results are shown in Table 6.
[Table 6]

TABLE 6

|  |  | Example 15 | | Comparative Example 9 | |
| --- | --- | --- | --- | --- | --- |
| Cp$_2$ZrCl$_2$ | (μmol) | 500 | | 500 | |
| MAO | (μmol) | 8000 | | 8000 | |
| Halogen- kind | | DEAC | | 0 | |
| containing amount | (μmol) | 1500 | | 0 | |
| modifier | | | | | |
| H$_2$ | (mL) | 0 | | 0 | |
| Solvent (toluene) | (mL) | 20 | | 20 | |
| Reaction temperature | (° C.) | 45 | | 45 | |
| Reaction time | (h) | 2 | 8 | 2 | 24 |
| Conversion | (%) | 56.9 | 96.8 | 33.8 | 97 |
| C$_{16}$ yield | (%) | 54.2 | 92.7 | 29.1 | 85.7 |
| C$_{16}$ selectivity | (%) | 95.3 | 95.8 | 86.1 | 88.4 |
| C$_{16}$ activity | (g C$_{16}$/h-mmol Zr) | 181.2 | 77.5 | 97.4 | 23.9 |
|  | (g C$_{16}$/h-mmol Al) | 11.3 | 4.8 | 6.1 | 1.5 |
| Vinylidene group ratio | (%) | | 99.7 | | 99.7 |

Comparative Example 9

A dimer (unsaturated hydrocarbon compound) was obtained in the same manner as in Example 15, except that a toluene solution of diethyl aluminum chloride was not added.

The results indicated that after 2 hours of reaction, the conversion of raw material 1-octene was 33.8 mol %, and the yield of the dimer was 29.8 mol %, and after 24 hours of reaction, the conversion of raw material 1-octene was 97.0 mol % and the yield of the dimer was 85.7 mol %.

An analysis by $^1$H-NMR indicated that the dimer contained 99.7 mol % of the unsaturated double bond (the ratio of vinylidene group was 95.1 mol %).

The results are shown in Table 6.

INDUSTRIAL APPLICABILITY

According to the present invention, there is produced an unsaturated hydrocarbon compound particularly having a terminal vinylidene group in a high yield and high selectivity, which is useful as a lubricant, a cleaning agent, a additive and an intermediate thereof.

The invention claimed is:

1. A method of producing an unsaturated hydrocarbon compound, comprising:
   dimerizing an α-olefin in the presence of a catalyst comprising a metallocene compound (A) and an oxygen-containing organometallic compound modified with a halogen-containing compound (B);
   wherein:
   the metallocene compound (A) is a compound represented by general formula (1)

$$Q_a(C_5H_{5-a-b}R^1{}_b)(C_5H_{5-a-c}R^2{}_c)M^1XY \quad (1)$$

wherein:
   Q represents a connecting group for crosslinking two conjugated 5-membered ring ligands $(C_5H_{5-a-b}R^1{}_b)$ and $(C_5H_{5-a-c}R^2{}_c)$;
   each of $R^1$ and $R^2$ independently represents a hydrocarbon group, a halogen atom, an alkoxy group, a silicon-containing hydrocarbon group, a phosphorus-containing hydrocarbon group, a nitrogen-containing hydrocarbon group, or a boron-containing hydrocarbon group;
   each $R^1$ and $R^2$ may be the same or different from one another when plural groups are present and may form a ring structure by bonding with one other;
   a is 0, 1 or 2;
   each of b and c is independently an integer of 0 to 5 when a=0, an integer of 0 to 4 when a=1, and an integer of 0 to 3 when a=2;
   $M^1$ represents a transition metal from Group 4 of the periodic table; and
   each of X and Y independently represents a covalent bond ligand or an ionic bond ligand, and X and Y may be bonded with each other;
   the oxygen-containing organometallic compound modified with the halogen-containing compound (B) is obtained by modifying an oxygen-containing organometallic compound represented by at least one of general formula (2) and general formula (3) with a halogen-containing compound

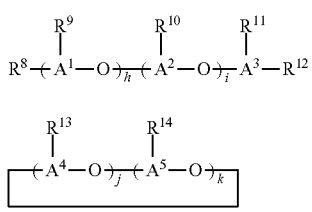

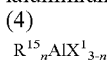

wherein:
each of $R^8$ to $R^{14}$ independently represents an alkyl group having 1 to 8 carbon atoms:
each of $A^1$ to $A^5$ independently represents a metal element from Group 13 of the periodic table;
each of h to k is independently a number of 0 to 50; and
each of (h+i) and (j+k) is larger than 1; and
the halogen-containing compound is a halogenated alkylaluminium compound represented by general formula (4)

$$R^{15}{}_n AlX^1{}_{3-n} \quad (4)$$

wherein:
$R^{15}$ represents a hydrocarbyl group having 1 to 20 carbon atoms or an organometalloid group;
$X^1$ represents a halogen atom; and
n satisfies the relation 0<n<3.

2. The method for producing an unsaturated hydrocarbon compound according to claim 1, wherein $M^1$ represents zirconium.

3. The method for producing an unsaturated hydrocarbon compound according to claim 1, wherein the α-olefin is dimerized in the presence of hydrogen.

4. The method for producing an unsaturated hydrocarbon compound according to claim 3, wherein at least 80 mol % of hydrocarbon compounds obtained by the method include at least one unsaturated double bond.

5. The method for producing an unsaturated hydrocarbon compound according to claim 1, wherein at least 80 mol % of hydrocarbon compounds obtained by the method include at least one unsaturated double bond.

6. The method for producing an unsaturated hydrocarbon compound according to claim 1, wherein the halogenated alkylaluminium compound represented by general formula (4) is:

selected from the group consisting of methylaluminum dichloride, ethylaluminum dichloride, n-propylaluminum dichloride, n-butylaluminum dichloride, isobutylaluminum dichloride, and tert-butyl aluminum dichloride when n=1;

selected from the group consisting of methylaluminum sesquichloride, ethylaluminum sesquichloride, n-propylaluminum sesquichloride, n-butylaluminum sesquichloride, isobutylaluminum sesquichloride, and tert-butylaluminum sesquichloride when n=1.5; and selected from the group consisting of dimethylaluminum chloride, diethylaluminum chloride, di-n-propylaluminum chloride, di-n-butylaluminum chloride, di-isobutylaluminum chloride, and di-tert-butylaluminum chloride when n=2.

7. The method for producing an unsaturated hydrocarbon compound according to claim 1, further comprising preparing the catalyst in a reactor at a temperature of −30 to 200° C.

8. The method for producing an unsaturated hydrocarbon compound according to claim 1, wherein:
the metallocene compound (A) is bis(cyclopentadienyl) zirconium dichloride;
the oxygen-containing organometallic compound is methylaluminoxane;
the halogen-containing compound is selected from the group consisting of dimethylaluminum chloride, ethylaluminum sesquichloride, dieethylaluminum chloride, and diisobutylaluminum chloride.

9. The method for producing an unsaturated hydrocarbon compound according to claim 8, wherein:
a molar ratio of the metallocene compound (A) to the oxygen-containing organometallic compound is from 1/1 to 1/100; and
a molar ratio of the metallocene compound (A) to the halogen-containing compound is from 1/0.5 to 1/100.

10. The method for producing an unsaturated hydrocarbon compound according to claim 9, wherein:
a molar ratio of the metallocene compound (A) to the oxygen-containing organometallic compound is from 1/2 to 1/100; and
a molar ratio of the metallocene compound (A) to the halogen-containing compound is from 1/1 to 1/20.

* * * * *